United States Patent
Westphal et al.

(10) Patent No.: US 9,549,672 B2
(45) Date of Patent: Jan. 24, 2017

(54) DEVICE AND METHOD FOR IMAGING AN OCULAR FUNDUS

(71) Applicant: CARL ZEISS AG, Oberkochen (DE)

(72) Inventors: Peter Westphal, Jena (DE); Daniel Bublitz, Rausdorf (DE)

(73) Assignee: Carl Zeiss AG, Oberkochen (DE)

(*) Notice: Subject to any disclaimer, the term of this patent is extended or adjusted under 35 U.S.C. 154(b) by 304 days.

(21) Appl. No.: 14/346,637

(22) PCT Filed: Sep. 21, 2012

(86) PCT No.: PCT/EP2012/068605
§ 371 (c)(1),
(2) Date: Mar. 21, 2014

(87) PCT Pub. No.: WO2013/041658
PCT Pub. Date: Mar. 28, 2013

(65) Prior Publication Data
US 2014/0232987 A1 Aug. 21, 2014

(30) Foreign Application Priority Data

Sep. 23, 2011 (DE) .................. 10 2011 053 880

(51) Int. Cl.
*A61B 3/14* (2006.01)
*A61B 3/00* (2006.01)
(Continued)

(52) U.S. Cl.
CPC ............. *A61B 3/12* (2013.01); *A61B 3/0008* (2013.01); *A61B 3/14* (2013.01); *A61B 3/158* (2013.01)

(58) Field of Classification Search
CPC ........... A61B 3/14; A61B 3/103; A61B 3/113; A61B 3/1225; A61B 3/024; A61B 3/1015
(Continued)

(56) References Cited

U.S. PATENT DOCUMENTS 5,426,623 A * 6/1995 Alon .................... G11B 7/0901
369/102
2008/0204762 A1 8/2008 Izatt et al.
(Continued)

FOREIGN PATENT DOCUMENTS

DE 199 20 158 A1 11/2000
DE 101 45 823 A1 4/2003
(Continued)

OTHER PUBLICATIONS

Gérald Lepage, Lou Harmans, CMOSIS NV, Antwerpen, Belgien, "TDI-Architekturen in CMOS-Bildaufnehmern", Photonik May 2009, S. pp. 34-37.

*Primary Examiner* — Dawayne A Pinkney
(74) *Attorney, Agent, or Firm* — Patterson Thuente Pedersen, P.A.

(57) ABSTRACT

An appliance for recording an image of an ocular fundus includes an irradiating device with a radiation source and optical components for generating an illumination strip. A scanning device is set up to cause a scanning movement of the illumination strip for the purpose of scanning the ocular fundus. An optoelectronic sensor senses detection light issuing from the ocular fundus. The optoelectronic sensor has a plurality of sensor rows and is set up such that charges contained in one sensor row are each shifted, with a time delay, into a further sensor row. A control means is connected to the scanning device and/or to the optoelectronic sensor and is set up to control the scanning movement and/or the time delay.

31 Claims, 8 Drawing Sheets

(51) Int. Cl.
*A61B 3/10* (2006.01)
*A61B 3/12* (2006.01)
*A61B 3/15* (2006.01)

(58) Field of Classification Search
USPC ........ 351/206, 200, 205, 209–211, 221–222, 351/246
See application file for complete search history.

(56) References Cited

U.S. PATENT DOCUMENTS

| | | | |
|---|---|---|---|
| 2009/0153798 A1* | 6/2009 | Dick | A61B 5/021 351/206 |
| 2009/0244482 A1 | 10/2009 | Elsner et al. | |
| 2010/0134802 A1* | 6/2010 | Chan | G01N 21/4795 356/497 |
| 2012/0327365 A1* | 12/2012 | Makihira | G06T 7/204 351/206 |

FOREIGN PATENT DOCUMENTS

| | | |
|---|---|---|
| DE | 10 222 779 A1 | 3/2004 |
| EP | 1 513 441 | 3/2005 |
| EP | 1 875 857 A1 | 1/2008 |
| WO | WO 00/54301 | 9/2000 |
| WO | WO 03/105679 | 12/2003 |
| WO | WO 2007/054301 A1 | 5/2007 |
| WO | WO 2008/003788 A2 | 1/2008 |
| WO | WO 2010/119750 A1 | 10/2010 |
| WO | WO 2011/099236 A1 | 8/2011 |

\* cited by examiner

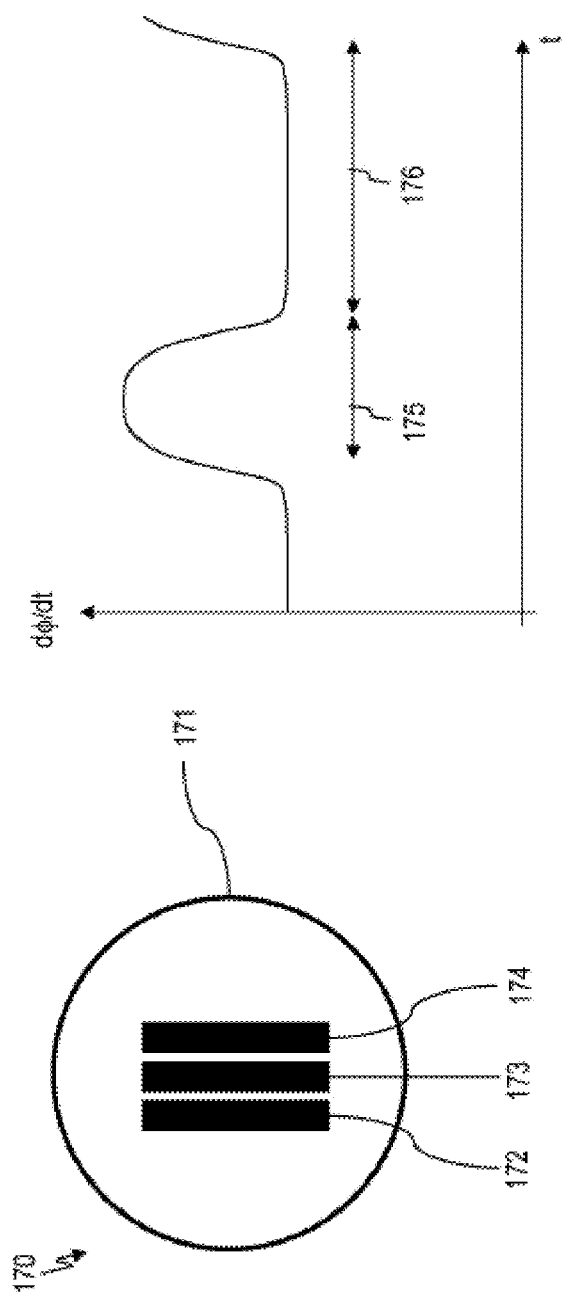
FIG. 8
FIG. 9
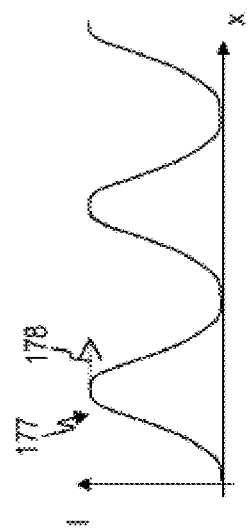
FIG. 10

DEVICE AND METHOD FOR IMAGING AN OCULAR FUNDUS

RELATED APPLICATIONS

The present application is a National Phase entry of PCT Application No. PCT/EP2012/068605, filed Sep. 21, 2012, which claims priority to DE Application No. 10 2011 053 880.1 filed Sep. 23, 2011, which applications are hereby incorporated by reference herein in their entirety.

FIELD OF THE INVENTION

The invention relates to devices and methods for imaging an ocular fundus. The invention particularly relates to devices and methods for imaging an ocular fundus which use an optoelectronic sensor for recording a digital image of the ocular fundus.

Devices and methods for imaging an ocular fundus are used for examining the eye, particularly the human eye. In the following, the ocular fundus ("fundus oculi") will also be called fundus. Devices and methods for imaging the ocular fundus are used, for example, for the diagnosis of diseases of a retina of an eye, particularly a human eye. For example, the use of so-called fundus cameras in combination with fluorescence and autofluorescence techniques for such purpose is known. Examples for applications are described in WO 2007/054301 A1, DE 10 222 779, DE 199 20 158, or DE 10 145 823.

Devices for imaging the ocular fundus include fundus cameras and ophthalmoscopes. A fundus camera has the distinction of having to ensure a specific optical resolution (60 line pairs/mm) and frequently having an annular illumination for suppressing reflections. In principle, ophthalmoscopes serve the same purpose but frequently have a smaller and technically simpler design.

Devices which image the ocular fundus in accordance with difference principles can differ from one another with regard to the type of illumination and the type of digital image acquisition.

Some devices for imaging the ocular fundus use annular illumination which is directed through the pupil of the eye in order to illuminate the fundus. A planar camera is used for detection through the non-illuminated center region of the pupil of the eye. The spatial separation of illumination and detection is necessary in order to sufficiently suppress reflections from the cornea and the crystalline lens in the fundus image. However, the numerical aperture for detection in such devices and methods can frequently be very small which limits the resolution. Furthermore, with this operating principle, fundus images can frequently be fraught with a high stray light background since wide-field detection is applied. This can lead to a relatively poor signal-to-background ratio in bright-field images or fluorescence images.

Devices for imaging the ocular fundus may also use transscleral illumination. This allows for an enlargement of the numerical aperture for the detection. Conventionally, a planar camera is used for detection. However, with many eyes, it is difficult to illuminate with blue and green light through the sclera since the absorption for those colors is too high. Such limitations can be undesirable.

A device for imaging the ocular fundus may also use or comprise a laser scanner. For example, such a device is described in EP 1 513 441 B1. The laser beam either impinges as point of light or line onto the ocular fundus. A single detector, for example a photomultiplier or a photodiode, can be used for detecting a point of light. If linear laser light is applied, a line scan camera can be used. Stray light can be suppressed with the use of a confocal aperture, providing for a satisfactory signal-to-background ratio. However, it is difficult with such a device to generate colored images of the ocular fundus at high quality. Since a laser radiation source is applied, there are spectral gaps even if a plurality of laser wavelengths is used for scanning. The use of continuum lasers would entail cost disadvantages.

WO 2008/003788 A1 describes a device for recording fundus images, using a pivotably mounted mirror for illumination. A camera with an electric aperture is used for detection using a spatially separate beam path. This movable aperture allows the electronic control of the temporally varying selection of the camera lines to be exposed. The spatial separation between illumination and detection limits the correspondingly available numerical aperture for illumination and detection.

SUMMARY OF THE INVENTION

A problem addressed by the invention is that of providing improved devices and methods for imaging the ocular fundus. The problem addressed by the invention is that of providing such improved devices and methods which do not require the spatial separation of illumination light and detection light in the eye and/or allow for imaging with illumination light of different wavelengths, particularly without major spectral gaps.

A device for imaging an ocular fundus according to one aspect comprises an irradiating device with a radiation source and optical components for generating an illumination strip. The device comprises a scanning device which is set up to cause a scanning movement of the illumination strip for the purpose of scanning the ocular fundus. The device comprises an optoelectronic sensor for recording the detection light originating from the ocular fundus. The optoelectronic sensor has a plurality of sensor rows and is set up such that charges contained in one sensor row are each shifted, with a time delay, into a further sensor row. The device has a controller which is coupled with the scanning device and/or the optoelectronic sensor and set up to control at least the scanning movement and/or the time delay.

The use of illumination, the intensity of which is concentrated on a strip-shaped region of the ocular fundus, allows for the suppression of stray light as compared to annular illumination or transscleral illumination. The use of the optoelectronic sensor, which is set up such that charges are shifted at a determined rate and/or a determined time delay from one sensor row to a further sensor row, allows for the accumulation of detection light while the illumination strip covers a section of the ocular fundus. The controller reduces or prevents a smearing of the image which is recorded during the scanning movement of the illumination strip over the ocular fundus.

The scanning device can be arranged in order to direct the detection light originating from the ocular fundus to the optoelectronic sensor. Due to such a so-called de-scanned geometry, illumination strip and detection light can pass through the same path. A separation of illumination and detection light is not necessary, and therefore a limitation of the numerical aperture caused by a separation of illumination and detection light can be prevented. Furthermore, such an arrangement ensures that the illumination strip always impinges on the same light-sensitive area of the optoelectronic sensor, achieving satisfactory use.

The controller can be set up to synchronize the time delay and a speed of the scanning movement. As a result, smears can be largely reduced or eliminated. The controller can be set up to synchronize such that a line on the ocular fundus is imaged in the same moving detector row of the optoelectronic sensor while the line from the illumination strip is covered.

The scanning device can have a pivotably mounted mirror. The controller can be set up to synchronize the time delay and an angular velocity of the mirror. The scanning device can have an actuator for the mirror. For example, the scanning device can be designed as galvanometer scanner (galvo scanner) or MEMS ("micro-electro-mechanical system") scanner. The controller can be coupled with the optoelectronic sensor and/or the actuator in order to adjust the synchronization between the scanning speed and the time delay, with which charges are each shifted between sensor rows of the optoelectronic sensor.

The device can be designed such that an angle between a first line, which corresponds to the propagation direction of the illumination light impinging on the mirror from the radiation source, and a second line, which connects the beam point of impact of the mirror with a center of an ophthalmoscope lens, is smaller or greater than 90°. This allows for particularly compact designs of the device.

The device can have a beam splitter, by application of which the illumination light is guided from the mirror to an ophthalmoscope lens. The beam splitter allows for the decoupling of light for a camera for recording an overview image.

The optical components of the irradiating device can be set up to adjust a width of the illumination strip such that an image of the illumination strip recorded by the optoelectronic sensor illuminates the plurality of sensor rows. This results in an integration of the detection light while the illumination strip covers a region of the ocular fundus.

The optical components of the irradiating device can be set up to adjust a width of the illumination strip such that a width, measured perpendicularly to the longitudinal direction of the illumination strip, on the ocular fundus is $1/1000$ to $1/10$ of the region of the ocular fundus to be imaged. Such a partial illumination leads to a decrease of the stray light background.

The optoelectronic sensor can comprise a TDI camera. Such a camera is also called a camera with time delay and integration. The TDI camera has a plurality of sensor rows. With a readout rate equal to that of the inverse time delay, an outer sensor row is read. The charges in the further sensor rows are each shifted, with a time delay, into the sensor row which is adjoining in the direction of the outer sensor row. Due to the use of the TDI camera, a sharp image of the ocular fundus can be generated even at a de-scanned geometry.

The TDI camera can be designed in CCD technology or CMOS technology. The TDI camera can be selected such that it has at least 10 sensor rows. The TDI camera can be selected such that it has no more than 500 sensor rows. The TDI camera can be designed such that every sensor row has at least 1000 pixels.

The TDI camera can be a monochrome TDI camera. Generally, a TDI camera is called a monochrome TDI camera if it only provides intensity information but no color information. The monochrome TDI camera can be sensitive to a plurality of different wavelengths in which the radiation source can generate light. If the radiation source is controlled such that different centroid wavelengths can be emitted time-sequentially, images for different wavelengths can be recorded time-sequentially with the monochrome TDI camera. The use of a monochrome TDI camera can be more cost-effective than the use of a color TDI camera which provides color resolution.

The TDI camera can also be a color TDI camera. It can comprise a plurality of camera chips and a plurality of filters assigned to said chips in order to record temporally parallel wavelength-resolved intensity information.

The device can comprise an arrangement for recording a stray light image, and a processing unit which is coupled with the optoelectronic sensor. The processing unit can be set up to computationally process an image of the ocular fundus recorded with the optoelectronic sensor, depending on the stray light image. This way, an image of the ocular fundus with further decreased stray light background can be computationally generated. The processing unit can be set up to subtract the stray light image from the image of the ocular fundus recorded with the optoelectronic sensor.

The arrangement for recording a stray light image can comprise at least one further TDI camera. The at least one further TDI camera can be arranged laterally offset to the optoelectronic sensor. The arrangement for recording a stray light image can comprise two further TDI cameras, each recording a stray light image. In such case, both stray light images can be subtracted from the image of the ocular fundus recorded with the optoelectronic sensor.

The at least one further TDI camera can be set up to record the stray light image simultaneously to the recording of the image of the ocular fundus with the optoelectronic sensor. Due to the temporally parallel recording with the primary optoelectronic sensor and the at least one further TDI camera, an extension of the data acquisition period can be prevented.

The arrangement for recording the stray light image can comprise at least one further radiation source, which is arranged offset to the radiation source. The controller can be coupled with the radiation source and the at least one further radiation source and can be set up to time-sequentially activate the radiation source and the at least one further radiation source. This allows for the recording of both the image of the ocular fundus and the stray light image with the optoelectronic sensor. The use of one or more further TDI cameras is possible but not necessarily required. This allows for a decrease of the number of optoelectronic sensors.

The processing unit can be set up to determine the stray light image from output data of the optoelectronic sensor if the at least one further radiation source is activated.

The radiation source can be set up to time-sequentially or simultaneously emit a plurality of, particularly at least three or at least four, different centroid wavelengths. The radiation source can be designed such that the different centroid wavelengths are each in one of the following spectral ranges: 400-500 nm, 500-600 nm, 600-700 nm, and 700-1000 nm. Controlling the radiation source allows for the control of the relative intensities of the different centroid wavelengths in order to record images of the ocular fundus with different illumination colors. Through time-sequential light emission with different centroid wavelengths, images of the ocular fundus can be recorded sequentially at different illumination wavelengths, for example with a monochrome TDI camera. Said images can be computationally processed. It is also possible to simultaneously emit a plurality of centroid wavelengths, wherein the image can be recorded with a color TDI camera.

The radiation source can comprise at least three independently switchable light-emitting diodes (LEDs), each forming a strip-shaped surface. For this purpose, three independently switchable LED chips can be attached to a base plate. The three LED chips which correspond to different centroid wavelengths can be independently switchable and dimmable. Each of the strip-shaped surfaces can be dimensioned such that their imaging on the ocular fundus corresponds to the illumination strip. Anamorphotic optics can be provided for adjusting the aspect ratio of the emitted illumination strip.

The irradiating device can be designed such that the illumination strip has an illumination structure along its longitudinal direction. The scanning device can be designed such that the structured illumination strip can be shifted laterally along the longitudinal direction of the illumination strip in the plane of the ocular fundus. A number of images which were each obtained for different lateral positions of the illumination structure can be computationally processed by a processing unit in order to decrease the stray light background.

The device can comprise an optical coherence tomographer (OCT). This allows for an additional depth-resolved measurement of ocular structures. The device can comprise a beam splitter for coupling measuring radiation of the means for optical coherence tomography into the beam path of the illumination light.

According to a further aspect, a method for imaging an ocular fundus is provided. An illumination strip is generated. A scanning movement of the illumination strip for scanning the ocular fundus is generated. Detection light originating from the ocular fundus is recorded with an optoelectronic sensor having a plurality of sensor rows, and charges contained in a sensor row are each shifted, with a time delay, into a further sensor row. At least either the scanning movement and the time delay are adjusted such that the time delay and the scanning movement are synchronized.

Embodiments of the method and each of the effects thus achieved correspond to the embodiments of the device.

The method can be performed with a device according to an aspect or embodiment.

BRIEF DESCRIPTION OF THE DRAWINGS

In the following, the invention shall be further described with reference to the attached drawing using embodiments.

FIG. 8 is a schematic depiction of a further radiation source of devices according to embodiments.

FIG. 9 shows schematically an angular velocity of a mirror of a device according to embodiments.

FIG. 10 illustrates an illumination structure imprinted onto an illumination strip.

DETAILED DESCRIPTION OF INVENTION

Figure 1:
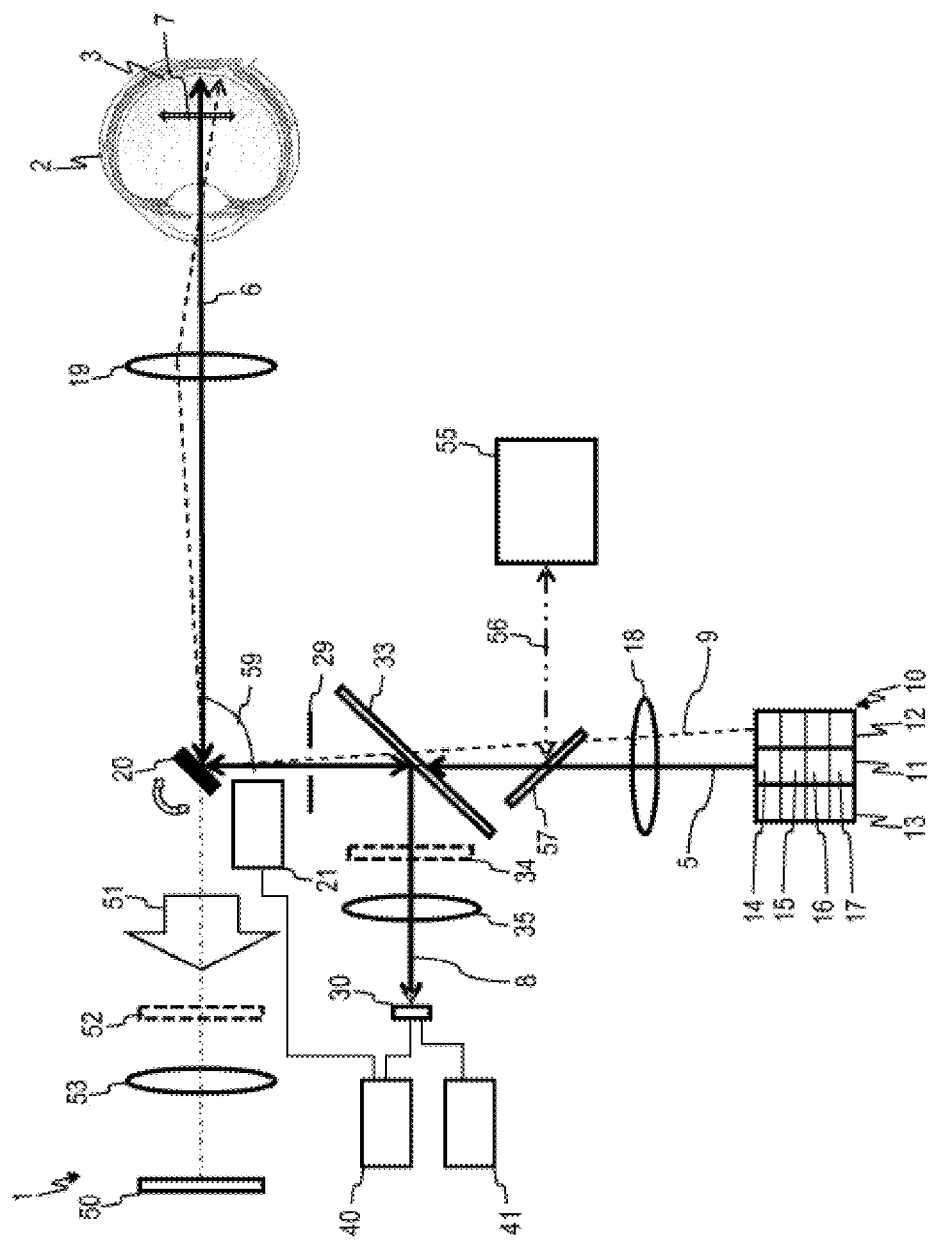
FIG. 1 is a schematic depiction of a device according to an embodiment.

In the following, embodiments of the invention are described in detail. The features of different embodiments can be combined with one another unless specified otherwise. The description of an embodiment which combines a number of features must not be interpreted such that all such features are required for the execution of the invention since other embodiments can have fewer features and/or alternative features.

In the drawings, similar or identical elements are denoted with similar or identical reference signs.

The embodiments described in the following relate to devices and methods for imaging an ocular fundus, for example, for funduscopy (ophthalmoscopy). An eye, particularly a human eye, is illuminated and the detection light originating from the ocular fundus is recorded. The device can be designed particularly such that the inside of the eye or the ocular fundus is illuminated through the pupil. Devices according to embodiments can be designed, for example, as fundus camera or ophthalmoscope.

With devices and methods according to embodiments, the ocular fundus is scanned with an illumination strip. An optoelectronic sensor, e.g. a TDI camera, with a plurality of sensor rows is used for the acquisition of images, wherein charges in a sensor row are shifted to a further sensor row where the accumulation of charges is continued and the light intensity thus received is integrated. These measures lead to a satisfactory imaging contrast without requiring a laser radiation source. Due to the utilization of TDI camera technology, sharp images can be recorded in an arrangement in which the detection light is directed onto the optoelectronic sensor by means of the scanning unit. The devices and methods according to embodiments, for example, can be used to record chromatic images of the ocular fundus and/or fluorescence images of the ocular fundus at high quality. The acquisition of such images can be combined with the acquisition of a near infrared (NIR) image of the ocular fundus for a time-dependent observation, for example, for focusing the ocular fundus.

FIG. 1 is a schematic depiction of a device 1 for imaging the ocular fundus according to an embodiment. The device 1 is used for imaging an ocular fundus or fundus 3 of an eye 2.

The device 1 comprises an illumination device 10 with a radiation source 11 and optical components for illuminating the ocular fundus with an illumination strip. The optical components, for example, can comprise first optics 18 and second optics 19. The second optics can be an ophthalmoscope lens. The optical components can also comprise an aperture 29 for adjusting a width of the illumination strip perpendicularly to its longitudinal direction.

The primary radiation source 11 is used for illuminating the ocular fundus for image acquisition. The radiation source 11 can be designed to sequentially or simultaneously emit at least three, particularly at least four different centroid wavelengths. A first centroid wavelength can be in the spectral range of 400-500 nm. A second centroid wavelength can be in the spectral range of 500-600 nm. A third centroid wavelength can be in the spectral range of 600-700 nm. A fourth centroid wavelength can be in the spectral range of 700-1000 nm. The radiation source 11 can be designed such that the spectral components with the different centroid wavelengths are controllably generated and emitted independently from one another. The radiation source 11 can be designed such that, optionally, blue, green, red, and near infrared radiation can be controllably radiated in various combinations onto the ocular fundus. The radiation source 11 can be designed such that the spectral components can be blended to white light. The radiation source 11 can comprise a plurality of different units 14-17 which are each designed to emit light with a centroid wavelength in one of the spectral ranges 400-500 nm, 500-600 nm, 600-700 nm, and 700-1000 nm. Embodiments of such radiation sources are described in detail with reference to FIGS. 6-8.

Figure 7:
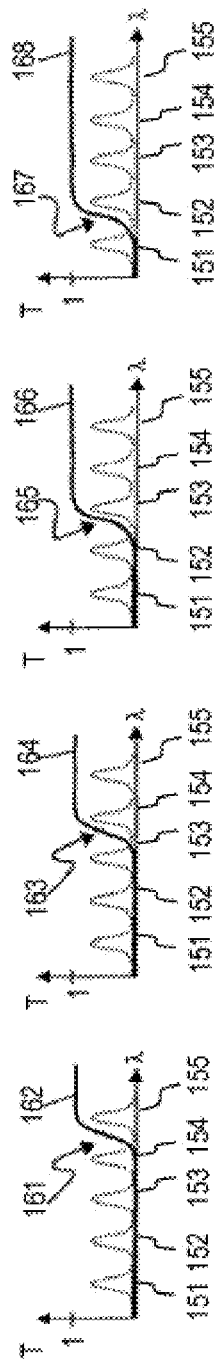
FIG. 7 is a schematic depiction of spectral components of radiation emitted by the radiation source in FIG. 6.

The device 1 comprises a scanning device for moving the illumination strip across the ocular fundus. The scanning device can comprise a movably mounted reflector, for example, a pivotably mounted mirror 20, and an actuator 21 for controllably adjusting the mirror 20. The scanning device, for example, can be designed as galvanometer scanner or MEMS scanner. The movement of the illumination strip, schematically depicted in FIG. 7, is perpendicular to the longitudinal direction of the illumination strip. The illumination strip in FIG. 1 extends perpendicularly to the drawing plane.

The mirror 20 can be positioned in or near a plane which is optically conjugated to the pupil of the eye. Thus, a transversal movement of the illumination strip in the fundus plane is generated with a change in the angle of the beam path on the mirror 20. The device 1 can be designed such that an angle 59 between the direction of incidence of the illumination strip impinging on the mirror 20 and the connecting line between the center of the illumination strip on the mirror 20 and an optical axis of the second optics 19 is greater or smaller than 90°. This allows for suppressing interfering reflections from the second optics 19 or from the eye 2. An angle 59 different from 90° can also allow for a more compact design of the device 1. In further embodiments of the invention, the angle 59 can, as depicted, be 90°.

The device 1 is designed such that the radiation 5 emitted from the radiation source 11 is directed onto the ocular fundus 3 by means of the mirror 20 of the scanning device using optics 18 and 19 such that a preferably homogenous, strip-shaped illumination is generated on said fundus 3. The illumination strip can be moved perpendicularly to its longitudinal axis by the scanning device over the ocular fundus 3 in order to scan the ocular fundus 3 by illuminating the regions of the ocular fundus 3 to be imaged. Using the aperture 29, the width of the illumination strip can be optionally adjusted from approximately ¹⁄₁₀₀₀ to approximately ¹⁄₁₀ of the fundus region to be imaged. This partial illumination allows for a reduction of the stray light background in comparison to an annular illumination or a transscleral illumination. The suppression factors, for example, can be within the range of 10 to 1000.

The device 1 comprises an optoelectronic sensor 30. Detection light originating from the ocular fundus 3 is guided to the optoelectronic sensor 30. Said detection light can run through the same beam path 6 as the illumination strip which is directed onto the ocular fundus 3. A spatial separation of illumination light and detection light on the eye is not required. The detection light can be guided by means of the second optics 19, the mirror 20 of the scanning device, and third optics 35 to the optoelectronic sensor 30. A beam splitter 33 can decouple the detection light 8 from the beam path of the illumination light and guide in the direction of the optoelectronic sensor 30. The third optics 35 can be arranged in the beam path from the beam splitter 33 to the optoelectronic sensor 30.

The beam splitters 33 and 57 can be color neutral or dichroic. The beam splitters 33 and 57 can be exchangeable by means of mechanical filters. This is advantageous if, during operation of the device 1, a change between reflection imaging and fluorescence imaging or between two different fluorescence wavelengths is required.

The optoelectronic sensor 30 is a planar sensor with a plurality of sensor rows. The optoelectronic sensor 30 is set up to successively image such regions of the ocular fundus 3 which are successively illuminated by the scanning device. The optoelectronic sensor 30 can be designed as so-called TDI ("time delay and integration") camera. The optoelectronic sensor 30 can have from 10 to 500 sensor rows.

The optoelectronic sensor 30 allows for a suppression of smears while the detection light is guided over the moving mirror 20 to the optoelectronic sensor 30. As will be further described with reference to FIG. 2, the optoelectronic sensor 30 is designed such that charges accumulated in a sensor row are shifted, with a time delay, into an adjoining sensor row where the accumulation of charges is continued. In an outermost sensor row, the charges are read. The time delay after which the charges are each shifted into the following sensor row is equal to the inverse readout rate.

Due to the de-scanned arrangement, which directs the detection light over the moving mirror 20 of the scanning device to the optoelectronic sensor 30, a stationary line on the ocular fundus 3 appears as moving object on the optoelectronic sensor 30. Due to the shifting of image information between sensor rows, a specific narrow strip of the moving object remains assigned to the moving sensor row. Thus, image information is accumulated until the image information is read at the last sensor row. This technology is advantageous over conventional cameras because a line-shaped segment of the ocular fundus can be sharply imaged with relatively long exposure time.

The optoelectronic sensor 30 can be designed as TDI camera with between 10 to 500 sensor rows, each of these having at least 1000, particularly several 1000 pixels. The optoelectronic sensor 30 can be a TDI camera manufactured with CCD technology. The CCD technology allows for easy implementation of the transfer of charges. The optoelectronic sensor 30 can be a TDI camera manufactured with CMOS technology. An example for such a TDI camera is described in Gérald Lepage, Lou Hermans, "TDI architectures in CMOS imaging devices," Photonik 5/2009, page 34.

As will be described in further detail, the optoelectronic sensor 30 can be designed as monochrome TDI camera. A color TDI camera can also be used. Such a color TDI camera can consist of a plurality of separate sensor chips with filters assigned to said chips. A monochrome TDI camera can be used particularly if the radiation source 11 is controlled such that light with different centroid wavelengths is emitted time-sequentially. The monochrome TDI camera then records color-sequential images which can be further processed with the processing unit 41. If white light is used for illumination, a color TDI camera is preferably used as optoelectronic sensor 30. A color TDI camera can have a color mask or consist of a plurality of monochrome TDI camera chips with the colored light assigned to said chips by means of color splitters. The TDI camera can also be particularly designed such that it detects radiation in the near infrared range (NIR radiation) which originates from the ocular fundus 3.

A controller 40 of the device 1 controls a rotary speed of the mirror 20 and/or the time delay or inverse readout rate with which the charges from sensor rows of the optoelectronic sensor 30 are each shifted to adjoining sensor rows. This results in a synchronization between the scanning speed and the shifting of charges between sensor rows. A stationary line on the ocular fundus, which is imaged by the mirror 20 of the scanning device onto different physical sensor rows of the optoelectronic sensor 30 while being covered by the illumination strip, can always be imaged onto the same moving sensor row. The integration of the optical signal results in a data acquisition with longer exposure time.

Read-out sensor rows can be assembled to an image by an electronic processing unit 41. The function of the controller 40 and the electronic processing unit 41 can be combined in a processor.

A so-called de-scanned arrangement is used in the device 1. Therefore, illumination beam path and imaging beam path are superimposed. A beam splitter 33 is used for directing the detection radiation onto the optoelectronic sensor 30. This arrangement ensures that the actually illuminated fundus region is always imaged on the sensitive surface of the optoelectronic sensor 30. In order to achieve a sharp image of the fundus, the row readout rate of the optoelectronic sensor 30 is adjusted to the scanning speed of the mirror 20. This measure allows for satisfactory suppression of the stray light background without the use of laser illumination. The use of illumination with spectral gaps which ordinarily occur with laser radiation sources is not required.

The device 1 can comprise a filter 34 in the path between the beam splitter 33 and the optoelectronic sensor 30. The filter 34 can be arranged such that it is selectively brought into the radiation path, for example, swiveled in. The filter 34 can be a band-elimination filter for the illumination radiation, thus also allowing for fluorescence images of the ocular fundus 3. The filter 34 can be designed, for example, for a fluorescence image of the autofluorescence of the ocular fundus or of dyes, e.g. fluorescein or ICG ("indocyanine green") which was injected in an examination object. The filter 34 and the beam splitter 33 can also be multiband filters in order to avoid a changing of the filter 34. The band-elimination filter allows for a further increase in contrast for fluorescence images of the ocular fundus.

The device 1 can comprise further optical units in order to record an overview image of the ocular fundus and/or a depth-resolved image of the eye. The mirror 20 of the scanning unit can be designed such that it allows radiation from the ocular fundus to pass past the side of the mirror 20. Alternatively, other arrangements can be used to record an overview image with a further optoelectronic sensor 50. The detection radiation can be used to obtain supplementary or redundant image information of the ocular fundus. Fur such purpose, optics 53 and the further optoelectronic sensor 50, as in a conventional fundus camera, can be additionally provided. Detection light 51 from the ocular fundus 3 is recorded by the further optoelectronic sensor 50 which can be an area detector. The further optoelectronic sensor 50, for example, can be a conventional planar camera chip in CCD or CMOS technology, wherein charges do not have to be shifted between detector rows. Such secondary imaging, for example, can be used to generate a NIR video image of the ocular fundus 3. This allows for the optimization of the detection using the optoelectronic sensor 30 for the visible range or for fluorescence images. Thus, a refocusing due to the large chromatic longitudinal error between the visible range and NIR can be foregone.

A further filter 52 can be provided in the path from the eye 3 to the further optoelectronic sensor 30. The filter 52 can be arranged such that it is selectively brought into the radiation path, for example, swiveled in. The filter 52 can be a band-elimination filter for the illumination radiation, thus making fluorescence images of the ocular fundus 3 possible. The filter 52 can be designed, for example, for a fluorescence image of the autofluorescence of the ocular fundus or of dyes, e.g. fluorescein or ICG ("indocyanine green").

The device 1 can also have a module 55 for optical coherence tomography (OCT). OCT measuring radiation 56 can be coupled into the beam path by means of a beam splitter 57 for depth-resolved measurement of ocular structures. With the use of the module 55 for optical coherence tomography, the distances between cornea, crystalline lens, and retina can be measured using OCT. Alternatively or additionally, it is also possible with the module 55 for optical coherence tomography to obtain spatially-resolved measurements of the morphologies of anterior chamber of the eye and retina using OCT. The OCT measuring radiation 56 can also be coupled at a point different from the one depicted in FIG. 1.

Devices according to embodiments, in which detection light from the ocular fundus is directed by means of the scanning device to an optoelectronic sensor which can be designed as TDI camera, can comprise additional elements and units for further stray light suppression. In this context, stray light is radiation which negatively impacts the quality of the imaging of the ocular fundus, particularly reflections from the boundary areas and scattered light from the crystalline lens or the vitreous humor. Such stray light poses a regular problem for the imaging of the ocular fundus.

The device 1 can have an arrangement for recording a stray light image which comprises at least one further radiation source 12, 13. The at least one further radiation source 12, 13 is arranged offset to the radiation source 11. Two further radiation sources 12, 13 can be used which are arranged laterally offset to the radiation source 11. The design of the further radiation sources 12 and 13 can each correspond to the design of the radiation source 11. The further radiation sources 12, 13 can each be set up to emit light with centroid wavelengths in a plurality of, particularly in at least three or at least four, spectral ranges. The further radiation sources 12, 13 can be designed to controllably generate and emit the spectral components with the different centroid wavelengths independently from one another. The further radiation sources 12, 13 can be designed such that that, optionally, blue, green, red, and near infrared radiation can be controllably radiated in various combinations onto the ocular fundus. The further radiation sources 12, 13 can be designed such that the spectral components, if required, can be blended to white light. The further radiation sources 12, 13 can each comprise a plurality of different units which are designed to emit light with a centroid wavelength in one of the spectral ranges 400-500 nm, 500-600 nm, 600-700 nm, and 700-1000 nm. Embodiments of such radiation sources are described in detail with reference to FIGS. 6-8.

During operation of the device 1, the controller 40 can control the radiation source 11 and the further radiation sources 12, 13 such that said sources emit light time-sequentially. The radiation 9 of the further radiation sources 12, 13 is directed to the ocular fundus by means of the first optics 18, the mirror 20 of the scanning device, and the second optics 19. An illumination strip is generated which, relative to the position of the illumination strip which would result from activating the radiation source 11 with the same position of the mirror 20, is offset in one direction perpendicular to the longitudinal direction of the illumination strip. The offset of the illumination strip can be caused by the transversal offset of the further radiation sources 12, 13 relative to the radiation source 11. Alternatively or additionally, optical elements can be provided for adjusting a desired offset for recording a stray light image. The illumination strip which is generated by activating one of the further radiation sources has the same dimensions as the illumination strip generated by activating the radiation source 11. If one of the further radiation sources 12 or 13 is activated, the detection light can, in turn, be recorded by the optoelectronic sensor 30. The offset of the illumination strip causes the stray light to impinge on the optoelectronic sensor 30, thus a stray light image can be recorded.

With the further radiation sources 12, 13, areas of the ocular fundus are illuminated, the detection light of which is not detected by the optoelectronic sensor 30 (at the same time). It is thus possible to measure one stray light image each from the ocular fundus with the optoelectronic sensor 30 in a separate measuring procedure during which the radiation source 11 is deactivated.

The electronic processing unit 41 can computationally process the data recorded by the optoelectronic sensor 30. The electronic processing unit 41 can make corrections for further suppressing the stray light background on an image of the ocular fundus which is recorded when the radiation source 11 is activated. Said correction can be made depending on a further image which is recorded when the further radiation source 12 is activated and/or depending on a further image which is recorded when the further radiation source 13 is activated. For example, the stray light images can be subtracted from the image of the ocular fundus which is recorded when the radiation source 11 is activated. The contrast can thus be further improved and/or reflections can be eliminated. The corrected image can be output to a user.

In the device 1 and the devices described with reference to FIGS. 3-5, an optoelectronic sensor, for example, a TDI camera, is used for image acquisition, wherein charges accumulated in sensor rows are each shifted, after a predetermined time interval, into the following sensor row where the accumulation of charges is continued. In an outermost sensor row, the charges are read. The cycle at which the charges are shifted between sensor rows is equal to the readout rate in the outermost sensor row. The controller 40 synchronizes the scanning movement and/or the time delay with which the charges accumulated in the sensor rows are each shifted into the following sensor row. A stationary line on the ocular fundus can thus always be imaged into the same moving sensor row. This results in a synchronicity in the shift of sensor rows and shift of the image of a stationary line on the ocular fundus caused by the de-scanned arrangement.

Figure 2:
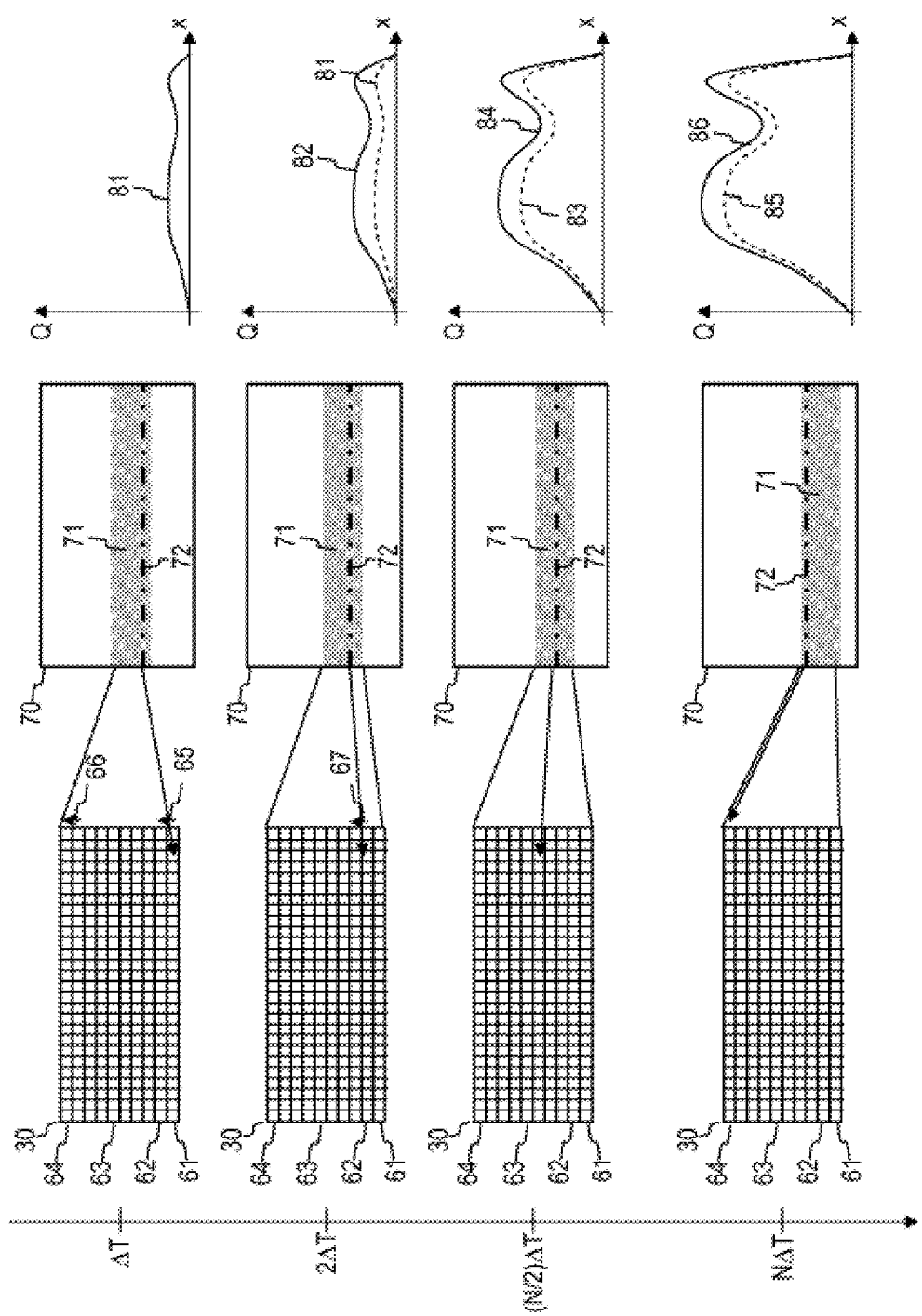
FIG. 2 is a schematic depiction for illustrating the action of an optoelectronic sensor in devices according to embodiments.

FIG. 2 is a schematic depiction for illustrating the action of an optoelectronic sensor 30 and the controller for synchronizing scanning movement and time delay. An area 70 of the ocular fundus is also depicted while an illumination strip 71 covers a line 72 of the ocular fundus. The charge accumulated in the moving sensor row, which is assigned to the line 72, is also depicted. Depicted are a number of points in time, each according to integral multiples of the time delay ΔT.

The optoelectronic sensor 30 has a plurality of sensor rows 61-64. The number of pixels per sensor row is greater, particularly much greater, than the number of sensor rows. Charges in the outermost sensor row 64 are each read. Charges in the other sensor rows are each shifted to the adjoining sensor row after the time interval ΔT.

In a first interval until the time t=ΔT, line 72 in the sensor row 61 is imaged. At the time t=ΔT, the charge 81, depicted as function of the pixel in the sensor row, is accumulated in the sensor row 61. After the time t=ΔT, the charges in all sensor rows, except for the sensor row 63, are shifted into the following sensor row, as depicted by the arrows 65, 66. The charges accumulated in the sensor row 61 are shifted into sensor row 62.

During the time interval from t=ΔT to t=2·ΔT, the line 72 is imaged in the sensor row 62 because the device is designed such that the time interval ΔT and the scanning movement of the mirror are synchronized. While the illumination strip continues to cover the line 72 during the time interval from t=ΔT to t=2·ΔT, the accumulation of charge in the sensor row 62 continues. At the time t=2·ΔΔT, the charge 82, depicted as function of the pixel in the sensor row, is accumulated in the sensor row 62. After the time t=2·ΔT, the charges in all sensor rows, except for the sensor row 64, are shifted into the following sensor row, as depicted by the arrows 67.

The shifting of charges at a cycle determined by the readout rate of outermost sensor row 64 is continued. Thus a moving sensor row is realized which follows the image of the line 72 on the optoelectronic sensor 30. For example, during the time interval t=(N/2)·ΔT, the line 72 is imaged in the sensor row 63, wherein N equals the number of sensor rows. While the maximum of the illumination strip continues to cover the line 72 in the time interval until t=(N/2)·ΔT, the accumulation of charge in the sensor row 63 continues. At the time t=(N/2)·ΔT, the charge 84 is accumulated in the sensor row 63, wherein the difference between the curves 84 and 83 corresponds to the integrated luminous power in the time interval from (N/2−1)·ΔT to (N/2)·ΔT.

At the time t=N·ΔT, the moving sensor line has reached the outermost physical sensor line 64. The accumulation of charge is continued in the sensor row 64 in the time interval until N·ΔT. At the time t=N·ΔT, the charge 86 is accumulated in the sensor row 63, wherein the difference between the curves 86 and 85 corresponds to the integrated luminous power in the time interval from (N−1)·ΔT to (N)·ΔT. At the time t=N·ΔT, the charges from the sensor row 64 are read.

Due to the shifting of charges to adjoining sensor rows, moving sensor rows are logically generated with the optoelectronic sensor, for example, a TDI camera. This results in a longer exposure time, wherein a movement-induced smearing is reduced or prevented due to the synchronization of readout rate and scanning speed.

The synchronization of readout rate and scanning speed can be realized in a variety of ways. The controller 40 can be coupled with the actuator 21 of the scanning device in order to adjust the movement of the mirror 20 on the basis of the readout rate of the optoelectronic sensor 30. The controller 40 can be coupled with the optoelectronic sensor 30 in order to adjust the readout rate and thus the time delay, based on which the charges are shifted from one sensor row to the next, on the basis of the rotary speed of the mirror 30 or on the basis of the motion speed of the illumination strip on the ocular fundus 7.

Different alternative or additional features can be implemented in devices according to embodiments.

Figure 3:
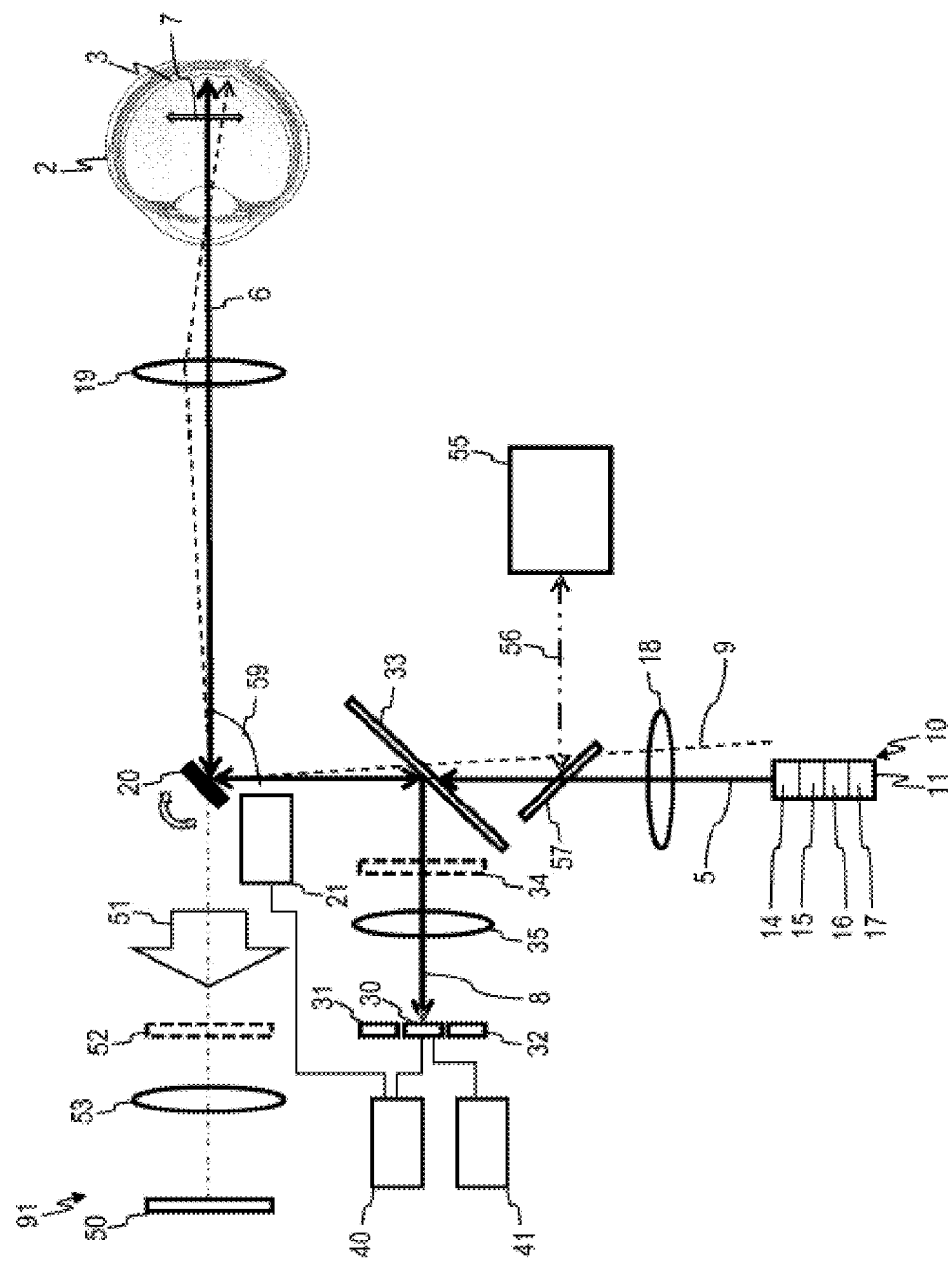
FIG. 3 is a schematic depiction of a device according to a further embodiment.

FIG. 3 is a depiction of a device 91 for imaging the ocular fundus according to an embodiment. Elements and arrangements which correspond to elements and arrangements of device 1 with regard to their function and design are denoted with the same reference signs.

Device 91 comprises an irradiating device 10 with a radiation source 11 and optical components 18, 19, a scanning device with a mirror 20, an optoelectronic sensor 30, and a controller 40. The optoelectronic sensor 30 has a plurality of sensor rows, wherein charges which are accumulated in sensor rows are shifted, each at the readout rate, into adjoining sensor rows and subsequently read from an outermost sensor row. The controller 40 controls the scanning speed and/or readout rate such that a moving, logical sensor row of the optoelectronic sensor 30 moves synchronously with the image of a line of the ocular fundus on the optoelectronic sensor 30.

The device 91 also has an arrangement for suppressing stray light which has a different design than in the device 1.

The arrangement for suppressing stray light comprises at least one further optoelectronic sensor 31, 32. The at least one further optoelectronic sensor 31, 32 is arranged offset to the optoelectronic sensor 30. Two further optoelectronic sensors 31, 32 can be used which are arranged laterally offset to the optoelectronic sensor 30. The further optoelectronic sensors 31, 32 can each be designed similar to the optoelectronic sensor 30. The further optoelectronic sensors 31, 32 can each be a sensor of a TDI camera.

During operation of the device 91, the optoelectronic sensors 31, 32, simultaneously to the image acquisition by the optoelectronic sensor 30, record stray light images. Due to the lateral shift, areas of the ocular fundus which are next to the illuminated strip are imaged on the optoelectronic sensors 31, 32. Therefore, one stray light image of the ocular fundus each can be measured by the optoelectronic sensors 31, 32. This stray light image can be subtracted from the image of the primary optoelectronic sensor 30 in order to improve contrast and/or eliminate reflections. The corresponding computational processing of the image of the primary optoelectronic sensor 30 can be executed by the electronic processing unit 41.

The device 1 or the device 91 can also be designed such that there are a plurality of radiation sources transversally offset to one another and a plurality of optoelectronic sensors according to the TDI principle which are transversally offset to one another. Correspondingly, the electronic processing unit 41 can computationally process the various recorded images in order to suppress the stray light background.

Figure 4:
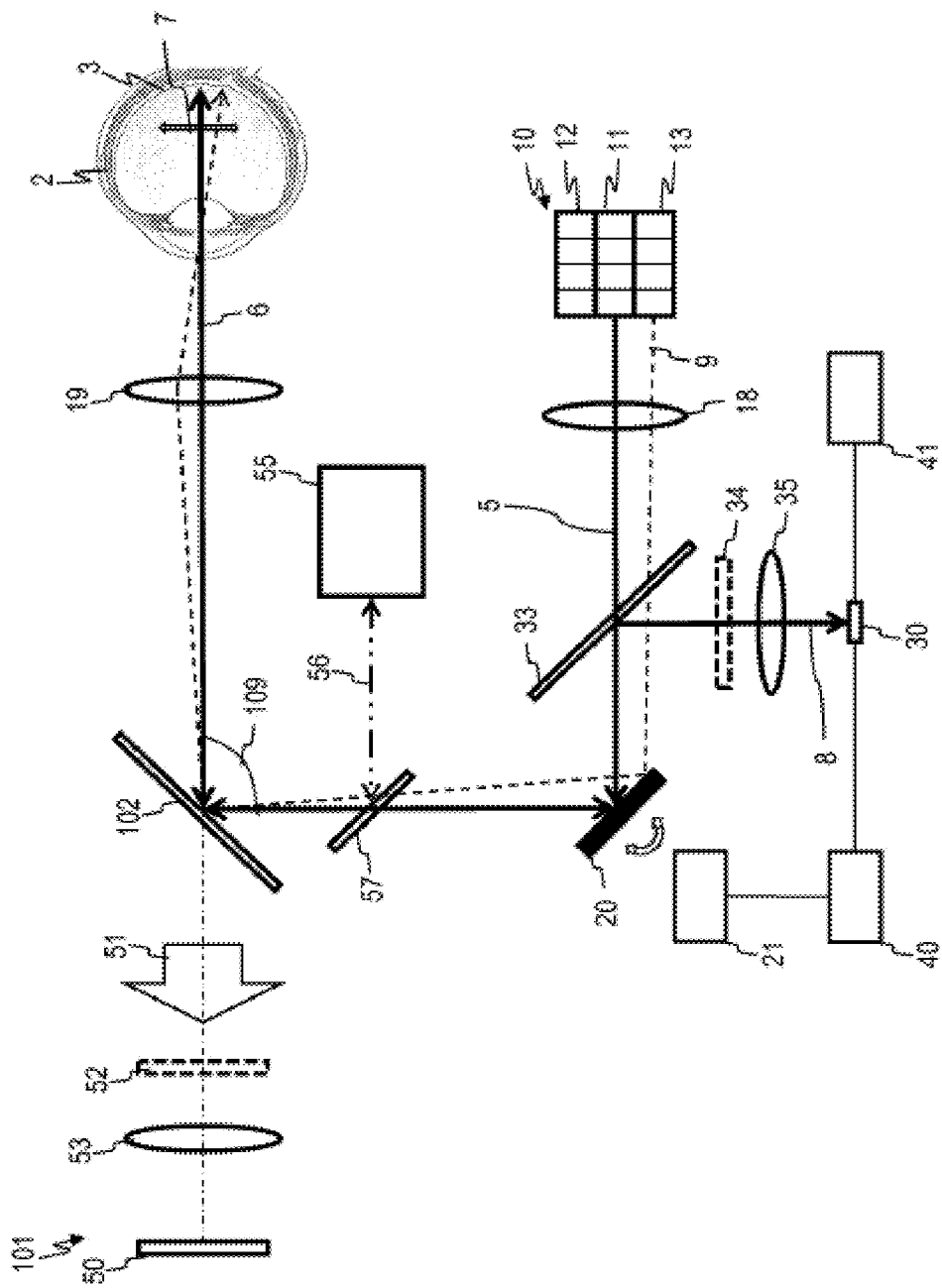
FIG. 4 is a schematic depiction of a device according to a further embodiment.

FIG. 4 is a depiction of a device 101 for imaging the ocular fundus according to an embodiment. Elements and arrangements which correspond to elements and arrangements of device 1 with regard to their function and design are denoted with the same reference signs.

The device 101 comprises an irradiating device 10 with a radiation source 11 and optical components 18, 19, a scanning device with a mirror 20, an optoelectronic sensor 30, and a controller 40. The optoelectronic sensor 30 has a plurality of sensor rows, wherein charges which are accumulated in sensor rows are each shifted, at the readout rate, into adjoining sensor rows and read from an outermost sensor row. The controller 40 controls the scanning speed and/or readout rate such that a moving, logical sensor row of the optoelectronic sensor 30 moves synchronously with the image of a line of the ocular fundus on the optoelectronic sensor 30.

In the device 101, a further beam splitter 102 is provided in the path between the mirror 20 of the scanning device and the second optics 19. This prevents a shadowing of the detection beam path 6 by the mirror 20 of the scanning device. This can be advantageous if a conventional fundus camera formed by optics 19, optics 53, and the optoelectronic sensor 50, is additionally used. With the embodiment according to the device 101, the interference of the beam path for the conventional fundus camera by the mirror 20 can be reduced or eliminated.

The beam path for the optoelectronic sensor 30 is coupled by means of the beam splitter 33. The beam splitter 33 can be dichroic in order to optimize light efficiency if different spectral ranges are to be recorded with the further optoelectronic sensor 50, i.e. the conventional planar camera, and the optoelectronic sensor 30.

With the device 101, an angle 109 which is formed by the connecting line between the centers of the mirror 20 and the beam splitter 102 and by the connecting line between the center of the beam splitter 102 and the second optics 19, can also be selected to be different from 90°. For example, this allows for better suppression of interfering reflections from the ophthalmoscope lens 19 or the eye. Alternatively or additionally, a more compact design of the device 101 can be realized.

The device 101 has further radiation sources 12, 13 which are, relative to the radiation source 11, laterally offset. By activating the further radiation sources 12 and/or 13, a stray light image can be recorded with the optoelectronic sensor 30. The processing unit 41 can computationally process the image, recorded by the optoelectronic sensor 30 through activation of the radiation source 11, in order to further reduce the stray light background. The processing unit 41 can be designed to subtract the stray light image recorded during activation of the further radiation source 12 and/or the stray light image recorded during activation of the further radiation source 13 from the image of the ocular fundus which is recorded during activation of the primary radiation source 11. The appropriate mode of operation corresponds to the mode of operation described with reference to FIG. 1.

Figure 5:
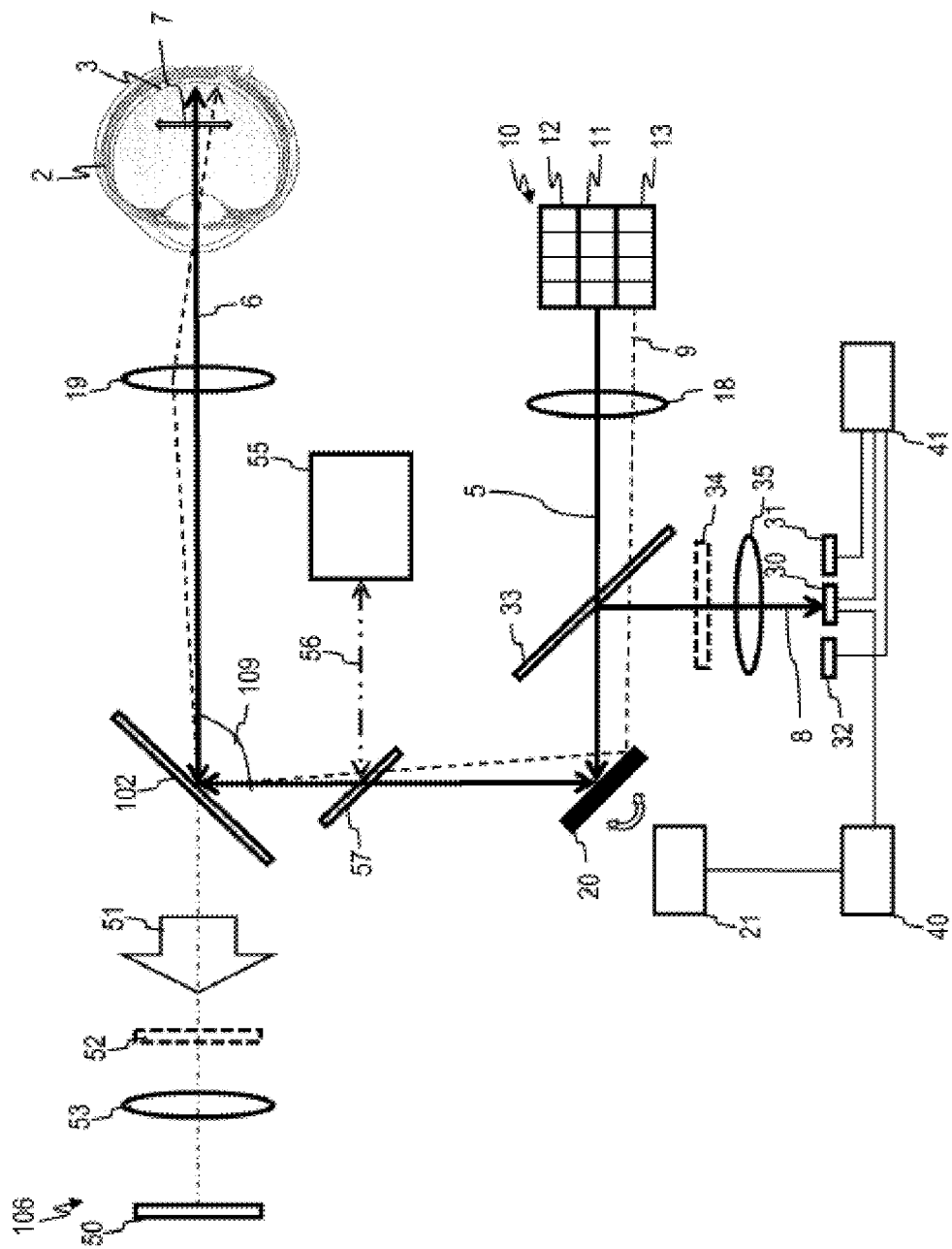
FIG. 5 is a schematic depiction of a device according to a further embodiment.

FIG. 5 is a depiction of a device 106 for imaging the ocular fundus according to an embodiment. Elements and arrangements which correspond to elements and arrangements of device 91 in FIG. 3 or device 101 in FIG. 4 with regard to their function and design are denoted with the same reference signs.

The device 106 comprises an irradiating device 10 with a radiation source 11 and optical components 18, 19, a scanning device with a mirror 20, an optoelectronic sensor 30, and a controller 40. The optoelectronic sensor 30 has a plurality of sensor rows, wherein charges which are accumulated in sensor rows are each shifted, at the readout rate, into adjoining sensor rows and read from an outermost sensor row. The controller 40 controls the scanning speed and/or readout rate such that a moving, logical sensor row of the optoelectronic sensor 30 moves synchronously with the image of a line of the ocular fundus on the optoelectronic sensor 30.

The device 106 has further optoelectronic sensors 31, 32 which are arranged transversally offset to the optoelectronic sensor 30. The further optoelectronic sensors can also operate according to the TDI principle. With the further optoelectronic sensors 31, 32 it is possible, temporally parallel to the image acquisition with the optoelectronic sensor 30, to record a stray light image while the primary radiation source 11 emits light. Stray light can be suppressed as described with reference to FIG. 3 through subtraction of the stray light image recorded with the further optoelectronic sensors 31, 32 from the image recorded with the optoelectronic sensor 30.

In addition, the device 106 can comprise a plurality of further radiation sources 12, 13 for suppressing stray light as described with reference to FIG. 1. In a further embodiment, the further radiation sources 12, 13 can be omitted.

In devices as described with reference to FIGS. 1-5, the radiation source and, if provided, the further radiation source(s) can be designed such that it (they) controllably emit a plurality of centroid wavelengths which lie in a plurality of, particularly in at least three, different spectral ranges. Embodiments of the radiation sources in devices according to embodiments are further described with reference to FIGS. 6-8.

Figure 6:
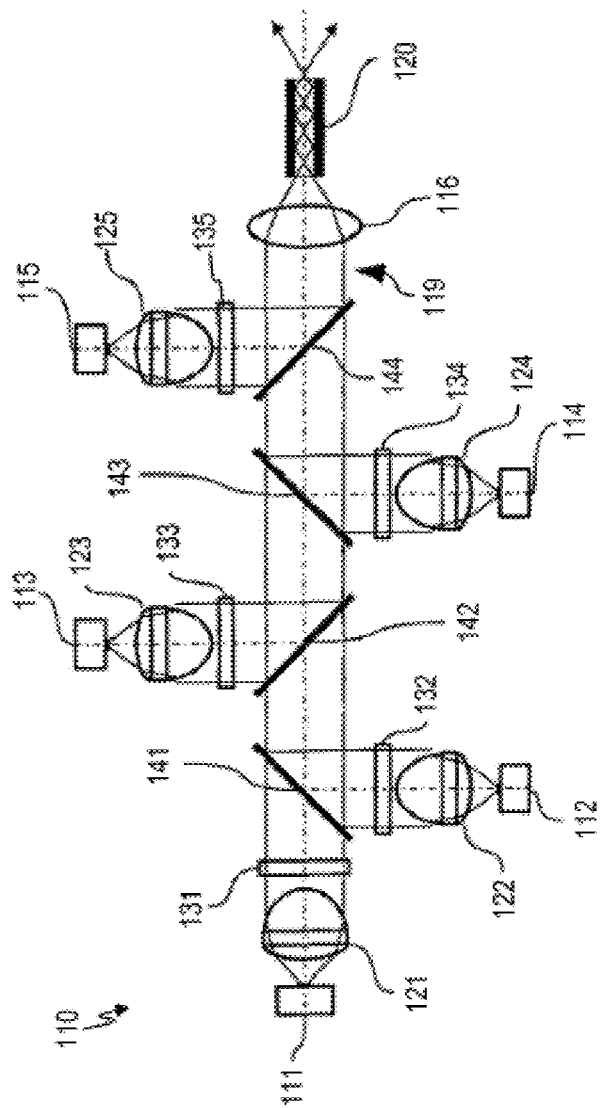
FIG. 6 is a schematic depiction of a radiation source of devices according to embodiments.

FIG. 6 is a schematic depiction of a radiation source 110 which is set up to sequentially or simultaneously emit a plurality of centroid wavelengths.

The radiation source 110 has a plurality of, particularly at least three, semiconductor radiation sources 111 to 115. The characteristic emission wavelengths of the emission spectra of the semiconductor radiation sources 111 to 115 are distributed differently and over the spectral range of at least the visible spectrum. One of the semiconductor radiation sources can be a radiation source for NIR radiation. One of the semiconductor radiation sources can be a radiation source for optical radiation in the UV range.

The semiconductor radiation sources can, for example, be selected in the form of light-emitting diodes. If the reference signs 111 to 115 each denote a semiconductor radiation source in an embodiment, the light-emitting diode 111, for example, can emit radiation with a characteristic emission wavelength in the IR or red range of the optical spectrum, the light-emitting diode 112 can emit radiation with a characteristic emission wavelength in the yellow range of the spectrum, the light-emitting diode 113 can emit radiation with a characteristic emission wavelength in the green range of the spectrum, and the light-emitting diode 114 can emit radiation with a characteristic emission wavelength in the blue range of the spectrum. A further light emitting diode 115 can emit radiation with a characteristic emission wavelength in the UV range.

The optical radiation of the semiconductor radiation sources 111 to 115 is coupled in the direction from the radiation source 111 to a homogenization device 120 successively by means of four corresponding color splitters 141 to 144, in a, e.g. linear, beam path from the radiation source 111 until past the color splitter 144, the output side of the beam path forming a common illumination beam path segment 119.

The four color splitters 141 to 144 can have a cascading transmission in the optical wavelength range. This is illustrated in FIG. 7 which, for the four color splitters, shows as a solid line the transmission 162, 164, 166, 168 of the corresponding color splitter 141-144 as a function of the wavelength, and the emission spectra 151-155 of the light-emitting diodes 111 to 115, i.e. their intensity as a function of the wavelength, as broken or dotted lines.

While the radiation of the light-emitting diode 111 is not deflected, the light-emitting diodes 112 to 115 are successively arranged along the beam path of the light-emitting diode 111 in a series of decreasing wavelengths, wherein the color splitters 141 to 144 are arranged tilted by 45° with respect to the linear beam path originating from the light-emitting diode 111 in order to couple the radiation of the light-emitting diodes 112 to 115 in the common illumination beam path segment 119.

A collimation device 121 to 125 is each arranged between the light-emitting diodes and the closest color splitters 141 to 144 positioned next in the beam path, and excitation filters 131 to 135 are arranged between the collimation devices and the color splitters which, except for the synchronization with the centroid wavelengths of the light-emitting diodes 111 to 115, are designed similar to the ones in the first embodiment.

The radiation from the common illumination beam path segment 119 directly reaches optics 116 which directs the illumination radiation beam to the entry surface of a homogenization device 120. In FIG. 7, the emission spectra 151-155 of the light-emitting diodes for each of the color splitters are depicted as dotted lines, and the transmission of the corresponding color splitter is depicted as solid line 162, 164, 166, 168. The filter edges or shoulders 161, 163, 165, 167 of the color splitters are arranged monotonically decreasing along the beam path originating from the light-emitting diode 111 in illumination direction as a function of the wavelength similar to those from the radiation source 111 to the homogenization device 120 of the light emitting diodes 36, and therefore radiation of the previous light-emitting diodes can pass but radiation of the next light-emitting diodes is deflected and coupled into the common beam path. Ideally, transmission of the color splitters in the intended pass band is 100% (T=1), and reflectivity below 45° in the same pass band is 0% (R=0), and vice versa.

The light-emitting diodes can also be arranged in reverse order, i.e. in an order of monotonically increasing centroid wavelengths, and so the light-emitting diode 115 has the greatest wavelength. In such case, the color splitters must be inverted with regard to their transmittance, i.e. transmission and reflection ranges are reversed. This implies that the color splitters are arranged in a series of monotonically increasing edge wavelengths along the illumination direction.

Other embodiments, as described in WO 2007/054301 A1, can also be used as the radiation source and/or the further radiation sources. These LED illumination arrangements are particularly suitable for illuminating the ocular fundus.

FIG. 8 shows an embodiment of a radiation source 170 which can be used in devices and methods according to embodiments. The radiation source 170 is designed as LED chip arrangement. The design can also be used for the further radiation sources of the device which can be provided for recording stray light images.

The radiation source 170 has three independently switchable and dimmable LED chips 172, 173, and 174 which are attached to a carrier 171, e.g. a base plate. Each of the LED chips 172, 173, 174 can be a strip-shaped homogenous radiating surface. The LED chips can be designed such that a high light density can be achieved. Every light strip can be formed from a plurality of smaller LED chips which are interconnected electronically in series or parallel. The light strips can be designed such that their imaging on the ocular fundus corresponds to the illumination strip which has the desired aspect ratio for imaging. If the aspect ratio of the light strips is different from the aspect ratio of the illumination strip in the ocular fundus, anamorphotic optics can be provided in the beam path in order to achieve the desired change of the aspect ratio of the illumination strip prior to impinging on the ocular fundus. The use of an aperture for the radiation source 170 is possible but not required.

In further embodiments, broadband and narrow-band radiation sources can be combined. For example, a white light source for color images of the ocular fundus and a NIR light-emitting diode for video imaging can be combined.

With radiation sources as described with reference to FIGS. 6-8, the light emission of the semiconductor elements, which have different centroid wavelengths, can be controlled such that only one semiconductor elements at a time emits light or that the radiation of the plurality of semiconductor elements is superimposed, for example, in order to generate white light. A time-sequential emission can be used particularly with a monochrome TDI camera. As a result, time-sequential images of the ocular fundus can be generated with different illumination. These images can be computationally combined by the processing unit 41. A broadband illumination is suitable for the use of color TDI cameras. For the radiation sources in FIGS. 6-8, a plurality of semiconductor elements can be simultaneously provided with current. Other radiation sources can be used, for example white light LEDs, flashbulbs, arc lamps, light bulbs, or continuum lasers (so-called white light lasers). Continuum lasers are more cost-intensive than the other radiation sources but have a significantly lower light conductance value. It is thus possible to generate very narrow illumination strips with high efficiency. Furthermore, due to the high bandwidth, continuum lasers are also well suited for OCT measurements with high depth resolution. For example, a single continuum laser can be used as radiation source for imaging with the optoelectronic sensor, which operates according to the TDI principle, and for imaging with the module 55 for optical coherence tomography.

In the devices according to the various embodiments, different embodiments of the scanning device can be utilized. For example, a rotatably mounted mirror 20 can be used. The movement for optical scanning of the ocular fundus can be executed with constant rotary speed of the mirror 20. The rotational direction can be reversed after every scan of the relevant area of the ocular fundus. Corresponding dead times resulting from the reversal of the rotational direction are taken into account by the control of the optoelectronic sensor 30. In order to decrease dead times, the rotary speed can also be periodically varied. For such purpose, the controller 40 can control the actuator 21 of the mirror 20 accordingly.

FIG. 9 shows schematically the adjusted angular velocity of the mirror 20 if said velocity is periodically varied. In an interval 175, the angular velocity can be changed in order to decrease or prevent dead times. In a further interval 176, the angular velocity can be kept mainly constant in order to achieve a predetermined motion speed of the illumination strip on the ocular fundus. The angular velocity can also be controlled such that the application of the angular position relative to the time results in a triangular or serrated course.

The readout rate of the optoelectronic sensor 30, which corresponds to the shift rate for the image information from row to row, is adjusted by the controller 40 in accordance with the appropriate speed or change in speed.

In the devices according to the different embodiments, an illumination strip can be used which is homogenous along its longitudinal direction. In further embodiments, a pattern which varies along the longitudinal direction can be imprinted onto the illumination strip.

FIG. 10 shows schematically such an intensity pattern 177 with the intensity of the illumination strip varying along a coordinate of its longitudinal direction. With the use of a thus structured illumination, an image of the ocular fundus can be recorded as described with reference to FIGS. 1-9, wherein the structured illumination is moved in one direction perpendicular to the longitudinal direction of the illumination strip. Subsequently, the structured illumination can be shifted in the plane of the ocular fundus along the longitudinal direction of the illumination strip, and the imaging can be repeated. The shifting of the illumination structure along the longitudinal direction is shown with 178. During imaging, the structured illumination is once again moved in one direction perpendicular to the longitudinal direction of the illumination strip. The images thus obtained for different positions of the illumination structure along the longitudinal direction of the illumination strip can be computationally combined. Due to imaging of a plurality of images of the ocular fundus at shifted illumination substructures, the stray light can subsequently be computationally eliminated from the resulting image.

Figure 11:
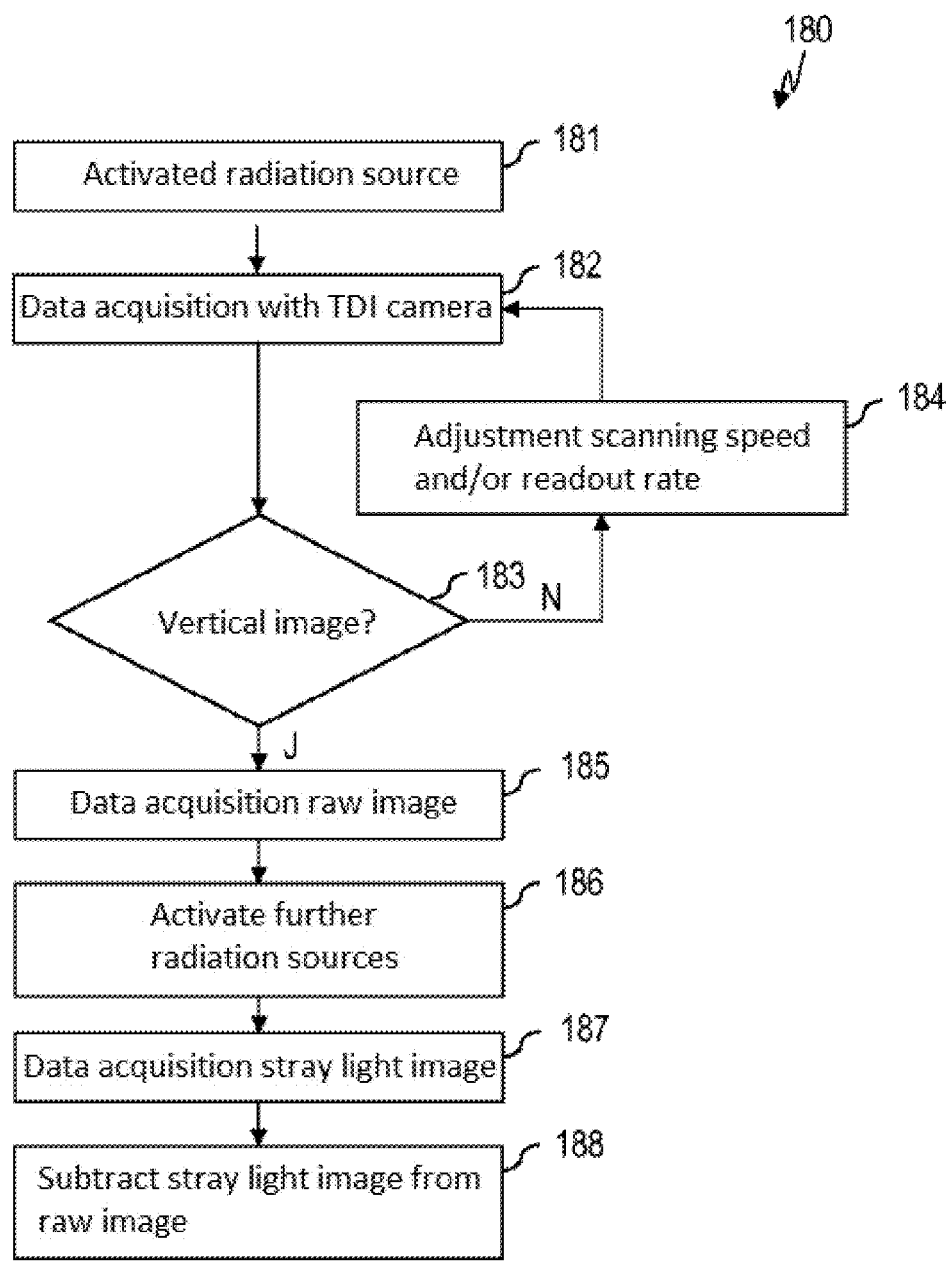
FIG. 11 is a flow chart of a method according to an embodiment.

FIG. 11 is a flow chart of a method 180 according to an embodiment. The method can be executed with a device according to an aspect or embodiment. The execution of the method can be automatically controlled by the controller of the device.

In step 181, a radiation source is activated. If a plurality of radiation sources is provided, as in device 1 in FIG. 1, device 101 in FIG. 4, or device 106 in FIG. 5, the primary radiation source 11 can be activated.

In step 182, data acquisition with a TDI camera is initiated. A preset value for the readout rate can be used which defines the time delay with which charges are shifted from row to row of the optoelectronic sensor.

In step 183, it is verified whether a vertical image was obtained for which the speed of the mirror 20 of the scanning device is synchronized with the time delay with which charges are shifted from row to row of the optoelectronic sensor. If it is determined in step 183 that no vertical image was obtained, the scanning speed of the scanning device and/or the readout rate of the optoelectronic sensor are adjusted in 184. The method returns to step 182.

If it is determined in step 183 that the speed of the mirror 20 of the scanning device is synchronized with the time delay with which charges are shifted from row to row of the optoelectronic sensor, a raw image is recorded in step 185. The value for the scanning speed and/or the readout rate is used, with which a moving row of the optoelectronic sensor follows the movement of a line of the ocular fundus which is imaged on the optoelectronic sensor. The radiated light can be broadband light having centroid wavelengths in a number of different spectral ranges. Alternatively, a plurality of images can be sequentially recorded for different wavelengths of the illumination.

For suppressing stray light effects, further steps can optionally be provided. For example, in step 186, the primary radiation source 11 can be deactivated and a radiation source 12 or 13, arranged offset from radiation source 11, can be activated. In step 187, data can be acquired once again with the optoelectronic sensor in order to record a stray light image. The value for the scanning speed and/or the readout rate is used, with which a moving row of the optoelectronic sensor follows the movement of a line of the ocular fundus which is imaged on the optoelectronic sensor.

In step 188, the raw image can be computationally processed on the basis of the stray light image. For example, the stray light image can be subtracted from the raw image in order to obtain an image of the ocular fundus with reduced stray light component. In order to not or only slightly increase image noise during subtraction, the high spatial frequencies can be eliminated from the stray light image prior to subtraction by means of filtration, e.g. a Fourier filtration.

For the method 180, steps 181-184 for synchronizing scanning speed and readout rate of the optoelectronic sensor do not have to be executed for every image. In fact, once determined parameters for imaging the ocular fundus can be used again. However, steps 181-184 can also be repeated, for example, for recalibrating the device.

While devices and methods were described according to embodiments, modifications can be realized in further embodiments.

While devices were described with a scanning device using a rotatably mounted mirror, other scanning devices can be utilized. For example, the device according to further embodiments can comprise a scanning device with a translationally adjustable mirror.

Devices according to embodiments can comprise a module for optical coherence tomography and/or a conventional planar image sensor for recording an overview image. In further embodiments, the module for optical coherence tomography and/or the planar image sensor for recording the overview image can be omitted.

Devices and methods allow for the use of radiation sources which overlap the visible spectrum without spectral gaps. Imaging with devices and methods can also be executed with the use of radiation sources which do not overlap the entire visible spectrum and/or have larger spectral gaps.

If a plurality of radiation sources and/or TDI cameras is provided for stray light suppression, they do not have to be arranged in a directly adjoining manner. For example, the further optoelectronic sensors and/or the further radiation sources used for suppressing stray light can be arranged separately from the primary optoelectronic sensor and/or primary radiation source. Suitable optical components can be used for adjusting the desired beam path for recording the stray light image.

Devices according to embodiments can be designed as appliances, wherein at least the irradiating device with the radiation source, the scanning device, and the optoelectronic sensor are fitted in a common housing. If an OCT measuring device is provided, it can be housed separately or in a common housing with the other components of the device for imaging an ocular fundus.

The invention claimed is:

1. A device for imaging an ocular fundus, comprising:
an irradiating device with a radiation source and optical components that generate an illumination strip;
a scanning device that is configured to cause a scanning movement of the illumination strip such that the illumination strip is scanned over the ocular fundus;
an optoelectronic sensor that records detection light originating from the ocular fundus;
wherein the optoelectronic sensor includes a plurality of sensor rows and is configured such that charges contained in one sensor row are each shifted, with a time delay, into a further sensor row; and
a controller which is operably coupled with the scanning device, the optoelectronic sensor or both the scanning device and the optoelectronic sensor and configured to control the scanning movement, the time delay or both the scanning movement and the time delay.

2. The device according to claim 1, wherein the scanning device is arranged to direct the detection light from the ocular fundus to the optoelectronic sensor.

3. The device according to claim 1, wherein the controller is configured to synchronize the time delay and a speed of the scanning movement.

4. The device according to claim 3, wherein the scanning device comprises a pivotably mounted mirror, and wherein the controller is configured to synchronize the time delay and an angular velocity of the mirror.

5. The device according to claim 1, wherein the optical components of the irradiating device are structured to adjust a width of the illumination strip such that an image of the illumination strip recorded by the optoelectronic sensor illuminates the plurality of sensor rows.

6. The device according to claim 1, wherein the optoelectronic sensor comprises a TDI camera.

7. The device according to claim 6, wherein the optoelectronic sensor comprises a monochrome TDI camera.

8. The device according to claim 1, further comprising: an arrangement that records a stray light image, and a processing unit that is coupled with the optoelectronic sensor and configured to computationally process an image of the ocular fundus recorded by the optoelectronic sensor, depending on the stray light image.

9. The device according to claim 8, wherein the arrangement for recording the stray light image comprises at least one further TDI camera.

10. The device according to claim 9, wherein the at least one further TDI camera is configured and arranged to record the stray light image simultaneously to the image of the ocular fundus recorded by the optoelectronic sensor.

11. The device according to claim 8,
wherein the arrangement for recording a stray light image comprises at least one further radiation source which is arranged offset to the radiation source; and
further wherein the controller is operably coupled with the radiation source and the at least one further radiation source and configured to activate the radiation source and the at least one further radiation source time-sequentially.

12. The device according to claim 9, wherein the arrangement for recording a stray light image comprises at least one further radiation source which is arranged offset to the radiation source; and
further wherein the controller is operably coupled with the radiation source and the at least one further radiation source and configured to activate the radiation source and the at least one further radiation source time-sequentially.

13. The device according to claim 11, wherein the processing unit is configured to determine the stray light image from output data of the optoelectronic sensor if the at least one further radiation source is activated.

14. The device according to claim 1, wherein the radiation source is configured to emit a plurality of different centroid wavelengths time-sequentially or simultaneously.

15. The device according to claim 1, wherein the radiation source is configured to emit at least four different centroid wavelengths time-sequentially or simultaneously.

16. The device according to claim 15, wherein the radiation source comprises at least three independently switchable and dimmable light-emitting diodes which each form a strip-shaped surface.

17. A method for imaging an ocular fundus, comprising:
generating an illumination strip;
causing a scanning movement of the illumination strip such that the illumination strip is scanned over the ocular fundus; and
recording detection light originating from the ocular fundus with an optoelectronic sensor which has a plurality of sensor rows and shifts, with a time delay, charges contained in one sensor row into a further sensor row;
wherein either the scanning movement, the time delay or both the scanning movement and the time delay are adjusted such that the time delay and the scanning movement are synchronized.

18. The method according to claim 17,
further comprising arranging a scanning device to direct the detection light from the ocular fundus to the optoelectronic sensor.

19. The method according to claim 17, wherein the scanning device comprises a pivotably mounted mirror, and further comprising synchronizing the time delay and an angular velocity of the mirror.

20. The method according to claim 17, adjusting a width of the illumination strip via optical components the such that an image of the illumination strip recorded by the optoelectronic sensor illuminates the plurality of sensor rows.

21. The method according to claim 17, further comprising configuring the optoelectronic sensor to comprise a TDI camera.

22. The method according to claim 21, further comprising configuring the optoelectronic sensor to comprise a monochrome TDI camera.

23. The method according to claim 17, further comprising: recording a stray light image, and computationally processing an image of the ocular fundus recorded by the optoelectronic sensor, depending on the stray light image by application of a processing unit which is coupled with the optoelectronic sensor.

24. The method according to claim 23, further comprising configuring an arrangement for recording the stray light image to comprise at least one further TDI camera.

25. The method according to claim 24, further comprising recording the stray light image simultaneously to the image of the ocular fundus recorded by the optoelectronic sensor by application of the at least one further TDI camera.

26. The method according to claim 23, further comprising arranging at least one further radiation source offset to the radiation source; and operably coupling a controller with the radiation source and the at least one further radiation source and activating the radiation source and the at least one further radiation source time-sequentially.

27. The method according to claim 24, further comprising the arranging at least one further radiation source offset to the radiation source; and activating the radiation source and the at least one further radiation source time-sequentially.

28. The method according to claim 27, further comprising determining the stray light image from output data of the optoelectronic sensor if the at least one further radiation source is activated.

29. The method according to claim 17, further comprising emitting a plurality of different centroid wavelengths time-sequentially or simultaneously from the radiation source.

30. The method according to claim 17, further comprising emitting at least four different centroid wavelengths time-sequentially or simultaneously from the radiation source.

31. The method according to claim 30, further comprising independently switching and dimming at least three independently switchable and dimmable light-emitting diodes to form a strip-shaped surface of the radiation source.

* * * * *

UNITED STATES PATENT AND TRADEMARK OFFICE
CERTIFICATE OF CORRECTION

PATENT NO.         : 9,549,672 B2
APPLICATION NO.    : 14/346637
DATED              : January 24, 2017
INVENTOR(S)        : Peter Westphal et al.

Page 1 of 1

It is certified that error appears in the above-identified patent and that said Letters Patent is hereby corrected as shown below:

In the Specification

Column 9, Line 40, delete "Fur" and insert --For--

Column 12, Line 3, delete the first "Δ"

In the Claims

Column 20, Line 57, Claim 20 delete the second occurrence of "the"

Signed and Sealed this
Fourteenth Day of August, 2018

Andrei Iancu
*Director of the United States Patent and Trademark Office*